(12) United States Patent
De Koker et al.

(10) Patent No.: US 11,684,577 B2
(45) Date of Patent: Jun. 27, 2023

(54) LIPID NANOPARTICLES

(71) Applicants: ETHERNA IMMUNOTHERAPIES NV, Niel (BE); Vrije Universiteit Brussel, Brussels (BE)

(72) Inventors: Stefaan De Koker, Niel (BE); Sanne Bevers, Niel (BE); Peter Tomme, Niel (BE)

(73) Assignees: ETHERNA IMMUNOTHERAPIES NV, Niel (BE); Vrije Unversiteit Brussel, Brussels (BE)

(*) Notice: Subject to any disclaimer, the term of this patent is extended or adjusted under 35 U.S.C. 154(b) by 0 days.

(21) Appl. No.: 16/961,843

(22) PCT Filed: Jan. 18, 2019

(86) PCT No.: PCT/EP2019/051261
§ 371 (c)(1),
(2) Date: Jul. 13, 2020

(87) PCT Pub. No.: WO2019/141814
PCT Pub. Date: Jul. 25, 2019

(65) Prior Publication Data
US 2020/0345641 A1    Nov. 5, 2020

(30) Foreign Application Priority Data

Jan. 18, 2018  (EP) .................... 18152390
Jan. 4, 2019   (EP) .................... 19150351

(51) Int. Cl.
*A61K 9/127*   (2006.01)
*A61K 31/7105* (2006.01)
*A61K 38/19*   (2006.01)

(52) U.S. Cl.
CPC ........ *A61K 9/1271* (2013.01); *A61K 31/7105* (2013.01); *A61K 38/19* (2013.01)

(58) Field of Classification Search
None
See application file for complete search history.

(56) References Cited

U.S. PATENT DOCUMENTS

2009/0004222 A1* 1/2009 O'Hagan ............. A61K 39/145
                                                 424/206.1
2011/0165223 A1* 7/2011 Sgouros ......... A61K 39/001195
                                                 424/450

(Continued)

FOREIGN PATENT DOCUMENTS

EP      2781507 B1    11/2012
WO    2012170889 A1   12/2012

(Continued)

OTHER PUBLICATIONS

Aude Bonehill, et al. "Enhancing the T-cell Stimulatory Capacity of Human Dendritic Cells by Co-electroporation With CD40L, CD70 and Constitutively Active TLR4 Encoding mRNA." Molecular Therapy, vol. 16 No. 6, Jun. 2008, pp. 1170-1180. (Year: 2008).*

(Continued)

*Primary Examiner* — Isaac Shomer
(74) *Attorney, Agent, or Firm* — Dinsmore & Shohl (57) ABSTRACT

The present invention relates to the field of lipid nanoparticles (LPN); more specifically comprising an ionisable lipid, a phospholipid, a sterol, a PEG lipid and one or more nucleic acids. The LNP's of the present invention are characterized in having a minimal average diameter of about 140 nm, thereby inducing a more potent immune response. The present invention provides use of the LNPs for immunogenic delivery of nucleic acid molecules, specifically mRNA; thereby making them highly suitable for use in vaccines, such as for the treatment of cancer or infectious diseases. Finally, methods are provided for preparing such LNP's.

16 Claims, 7 Drawing Sheets

(56) References Cited

U.S. PATENT DOCUMENTS

| | | | | |
|---|---|---|---|---|
| 2012/0276209 | A1* | 11/2012 | Cullis | C12N 15/111 424/490 |
| 2016/0250323 | A1* | 9/2016 | Sahin | A61P 35/00 424/450 |
| 2017/0340724 | A1* | 11/2017 | Ciaramella | A61K 39/12 |
| 2018/0155304 | A1* | 6/2018 | Nakai | A61K 9/1272 |

FOREIGN PATENT DOCUMENTS

| | | | | |
|---|---|---|---|---|
| WO | WO-2012170930 | A1* | 12/2012 | A61P 3/00 |
| WO | WO-2016121942 | A1* | 8/2016 | A61K 31/713 |
| WO | 2017062513 | A1 | 4/2017 | |
| WO | 2017192470 | A1 | 11/2017 | |
| WO | WO-2019077053 | A1* | 4/2019 | A61K 9/1272 |

OTHER PUBLICATIONS

Hidetaka Akita, et al. "Molecular Tuning of a Vitamin E-Scaffold pH-Sensitive and Reductive Cleavable Lipid-like Material for Accelerated in Vivo Hepatic siRNA Delivery." ACS Biomaterials Science and Engineering, vol. 1, 2015, pp. 834-844. (Year: 2015).*

Derek Lowe. "In the Pipeline: mRNA Vaccines: What Happens." https://blogs.sciencemag.org/pipeline/archives/2021/01/21/mrna-vaccines-what-happens accessed Apr. 19, 2021, originally published Jan. 21, 2021, pp. 1-30. (Year: 2021).*

Norbert Pardi et al. "Expression kinetics of nucleoside-modified mRNA delivered in lipid nanoparticles to mice by various routes." Journal of Controlled Release, vol. 217, 2015, pp. 345-301. (Year: 2015).*

Anil B. Jindal. "Nanocarriers for spleen targeting: anatomo-physiological considerations, formulation strategies and therapeutic potential." Drug Delivery and Translational Research, vol. 6, 2016, pp. 473-485. (Year: 2016).*

Norbert Pardi, Michael J. Hogan, Frederick W. Porter and Drew Weissman. "mRNA vaccines—a new era in vaccinology." Nature Reviews Drug Discovery, vol. 17, 2018, pp. 261-279, published online Jan. 12, 2018. (Year: 2018).*

Patrick Midoux and Chantal Pichon. "Lipid-based mRNA vaccine delivery systems." Expert Review of Vaccines, vol. 14(2), 2015, pp. 221-234. (Year: 2015).*

Linde Schoenmaker, Dominik Witzigmann, Jayesh A. Kulkarni, Rein Verbeke, Gideon Kersten, Wim Jiskoot, Daan J.A. Crommelin. "mRNA-lipid nanoparticle COVID-19 vaccines: Structure and stability." International Journal of Pharmaceutics 601 (2021) 120586, pp. 1-13. (Year: 2021).*

International Search Report and Written Opinion dated Mar. 26, 2019 for Application No. PCT/EP2019/051261.

Extended European Search Report dated Jul. 17, 2018 for Application No. 18152390.3.

Akita, et al., "Effect of hydrophobic scaffold on the cellular uptake and gene transfection activities of DNA-encapsulating liposomal nanoparticles via intracerebroventricular administration", International Journal of Pharmaceutics, Elsevier, vol. 490, No. 1, pp. 142-145, May 21, 2015, XP029179811.

Akita, et al., "A neutral lipid envelope-type nanoparticle composed of a pH-activated and vitamin E-scaffold lipid-like material as a platform for a gene carrier targeting renal cell carcinoma", Journal of Controlled Release, vol. 200, pp. 97-105, Dec. 24, 2014, XP029222024.

Kaufmann, et al., "Efficacy and immunogenicity of unmodified and pseudouridine-modified mRNA delivered systemically with lipid nanoparticles in vivo", Biomaterials, Elsevier, vol. 109, pp. 78-87, 2016.

Li, et al., "An Orthogonal Array Optimization of Lipid-like Nanoparticles for mRNA Delivery in Vivo", Supporting Information, pp. S1-S14, 2015.

Liang, et al., Efficient Targeting and Activation of Antigen-Presenting Cells in Vivo after Modicfied mRNA Vaccine Administration in Rhesus Macaques, Molecular Therapy, vol. 25, No. 12, pp. 2635-2647, Dec. 2017.

Reichmuth, et al., "mRNA vaccine delivery using lipid nanoparticles", Therapeutic Delivery, pp. 319-334, 2016.

Richner, et al., "Modifed mRNA Vaccines Protect against Zika Virus Infection", Cell Article, vol. 168, pp. 1114-1125, Mar. 9, 2017.

Thess, et al., "Sequence-engineered mRNA Without Chemical Nucleoside Modifications Enables an Effective Protein Therapy in Large Animals", The American Society of Gene and Cell Therapy, vol. 23, No. 9, pp. 1456-1464, Sep. 2015.

Lee et al., Microfluidic Mixing: A Review, International Journal of Molecular Sciences, vol. 12, pp. 3263-3287, 2011.

* cited by examiner

LIPID NANOPARTICLES

FIELD OF THE INVENTION

The present invention relates to the field of lipid nanoparticles (LNP); more specifically comprising an ionisable lipid, a phospholipid, a sterol, a PEG lipid and one or more nucleic acids. The LNP's of the present invention are characterized in having a minimal average diameter of about 140 nm, thereby inducing a more potent immune response. The present invention provides use of the LNPs for immunogenic delivery of nucleic acid molecules, specifically mRNA; thereby making them highly suitable for use in vaccines, such as for the treatment of cancer or infectious diseases. Finally, methods are provided for preparing such LNP's.

BACKGROUND TO THE INVENTION

One of the major challenges in the field of targeted delivery of biologically active substances is often their instability and low cell penetrating potential. This is specifically the case for the delivery of nucleic acid molecules, in particular (m)RNA molecules. Therefore, proper packaging is crucial for adequate protection and delivery. Hence, there is a continuous need for methods and compositions for packaging biologically active substances, such as nucleic acids.

In that respect, lipid-based nanoparticle compositions such as lipoplexes and liposomes have been used as packaging vehicles for biologically active substances to allow transport into cells and/or intracellular compartments. These lipid-based nanoparticle compositions typically comprise a mixture of different lipids such as cationic lipids, ionizable lipids, phospholipids, structural lipids (such as sterols or cholesterol), PEG (polyethylene glycol) lipids, . . . (as reviewed in Reichmuth et al., 2016). While many of such lipid compositions are known in the art, these typically have a small diameter, i.e. less than 200 nm, most often even less then 140 nm.

Lipid based nanoparticles composed of a mixture of 4 lipids—a cationic or ionizable lipid, a phospholipid, a sterol and a PEGylated lipid—have been developed for the non-immunogenic delivery of siRNA and mRNA to the liver after systemic administration. To evoke optimal hepatocyte uptake and expression, these LNPs typically display small sizes between 70-100 nm (Li et al., Nanoletters 2015; Thess et al. Mol ther 2015; Kauffman et al. Biomaterials 2016).

Beyond liver targeting, LNPs have also been used for the immunogenic delivery of antigen encoding mRNA to the muscle or dermis (Richner et al. Cell 2017; Liang et al., Mol Ther 2017). In this case, again small size (80-120 nm) LNPs are typically used since such small sizes have been shown to be crucial for immunogenicity, and small sized LNPs efficiently reach the injection draining lymph node, whereas larger LNP's are retained at the injection site (see Reichmuth et al., 2016).

We have now surprisingly found that in contrast to the general belief that small-sized particles are beneficial for LNP mediated mRNA delivery, nanoparticles having a diameter of more than 140 nm, preferably even more than 200 nm are highly suitable for immunogenic delivery of mRNA upon systemic injection of the LNPs, which appears to correlate with an enhanced delivery of mRNA to the spleen.

SUMMARY OF THE INVENTION

In a first aspect, the present invention provides a lipid nanoparticle (LNP) comprising an ionisable lipid, a phospholipid, a sterol, a PEG lipid and one or more nucleic acid molecules; characterized in that said LNP has a minimal average diameter of about 140 nm; more preferably of about 200 nm.

In a specific embodiment, said ionisable lipid is a compound of formula (I):

wherein:
RCOO is selected from the list comprising: myristoyl, α-D-Tocopherolsuccinoyl, linoleoyl and oleoyl; and
X is selected from the list comprising:

More specifically, said ionisable lipid is a lipid of formula (I) wherein RCCO is α-D-Tocopherolsuccinoyl and X is In a further embodiment of the present invention, said sterol is selected from the list comprising cholesterol, ergosterol, campesterol, oxysterol, antrosterol, desmosterol, nicasterol, sitosterol and stigmasterol; preferably cholesterol.

In another specific embodiment, said phospholipid is selected from the list comprising: 1,2-Dioleoyl-sn-glycero-3-phosphoethanolamine (DOPE), 1,2-Dioleoyl-sn-glycero-3-phosphocholine (DOPC), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhernisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In a more specific embodiment, said phospholipid is selected from the list comprising: 1,2-Dioleoyl-sn-glycero-3-phosphoethanolamine (DOPE), 1,2-Dioleoyl-sn-glycero-3-phosphocholine (DOPC), and mixtures thereof.

In yet a further embodiment, said PEG lipid is selected from the list comprising: PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In another specific embodiment, one or more of the following applies:
- said LNP comprises about and between 10 mol % and 60 mol % of said ionisable lipid;
- said LNP comprises about and between 15 mol % and 50 mol % of said sterol;
- said LNP comprises about and between 0.5 mol % and 10 mol % of said PEG lipid; and/or
- said LNP comprises about and between 5 mol % and 40 mol % of said phospholipid.

In another specific embodiment, said one or more nucleic acid molecules, are selected from (m)RNA and DNA molecules; more in particular one or more mRNA molecules. In a specific embodiment, said one or more mRNA molecules are selected from the list comprising mRNA molecules encoding immunomodulatory polypeptides such as (add a list of all potential molecules) and/or mRNA molecules encoding antigen- and/or disease-specific mRNA. In a very specific embodiment, said one or more mRNA molecules are selected from the list comprising mRNA molecules encoding for CD40L, CD70 and caTLR4; and/or mRNA molecules encoding antigen- and/or disease-specific mRNA.

The present invention also provides a pharmaceutical composition or a vaccine comprising one or more LNP's as defined herein.

Furthermore, the present invention provides an LNP as defined herein or a pharmaceutical composition comprising one or more of such LNP's for use in human or veterinary medicine.

In a further aspect, the present invention provides a method for the preparation of an LNP according to the invention, comprising:
- preparing a first alcoholic composition comprising said ionisable lipid, said phospholipid, said sterol, said PEG lipid, and a suitable alcoholic solvent;
- preparing a second aqueous composition comprising said one or more nucleic acids and an aqueous solvent;
- mixing said first and second composition in a in a microfluidic mixing device using the following settings:
  - Total Flow Rate (FR) of about 0.5 to about 8 ml/min, preferably of about 1 to 4 ml/min.
  - Flow Rate Ratio (FRR) of about 1/1 to 5/1, preferably of about 2/1 to about 3/1.

In a specific embodiment, said alcoholic solvent is ethanol and/or said aqueous solvent is water.

The present invention further provides the use of an LNP, a pharmaceutical composition or a vaccine according to the present invention for the immunogenic delivery of said one or more nucleic acid molecules.

Finally, the present invention provides an LNP, a pharmaceutical composition, or a vaccine as herein for use in the prevention and/or treatment of cancer or infectious diseases.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

As already detailed herein above, the present invention provides LNP's having a diameter which is larger than generally used in the field, for which we have surprisingly found that these are highly suitable for immunogenic delivery of nucleic acid, specifically mRNA; for which we found a correlation with enhanced delivery to the spleen. "immunogenic delivery of nucleic acid molecules" means delivery of nucleic acid molecules to cells whereby contact with cells, internalization and/or expression inside the cells of said nucleic acids molecules result in induction of an immune response.

Therefore, in a first aspect, the present invention provides a lipid nanoparticle (LNP) comprising an ionisable lipid, a phospholipid, a sterol, a PEG lipid and one or more nucleic acid molecules; characterized in that said LNP has a minimal diameter of about 140 nm; more preferably of about 200 nm.

A lipid nanoparticle (LNP) is generally known as a nanosized particle composed of a combination of different lipids. While many different types of lipids may be included in such LNP, the LNP's of the present invention are typically composed of a combination of an ionisable lipid, a phospholipid, a sterol and a PEG lipid.

As used herein, the term "nanoparticle" refers to any particle having a diameter making the particle suitable for systemic, in particular intravenous administration, of, in particular, nucleic acids, typically having a diameter of less than 1000 nanometers (nm).

In some embodiments, a nanoparticle has an average diameter of less than 600 nm. In some embodiments, a nanoparticle has an average diameter of less than 400 nm, but in any case the nanoparticles of the present invention have an average diameter of more than about 140 nm, more preferably more than about 200 nm. In a specific embodiment, the LNP's of the invention have a minimal average diameter of about 140 nm, about 150 nm, about 160 nm, about 170 nm, about 180 nm, about 190 nm or about 200 nm.

For the sake of clarity, where a mixture of multiple LNP's is used, the minimal average diameter as referred to, is meant to be the minimal average diameter of said multiple LNP's. In said instance, for example the mixture may contain some LNP's having a smaller average diameter than 140 nm, in as far as the remainder of the LNP's has an average diameter larger than 140 nm to result in an average minimum diameter of 140 nm of all LNP's together. Whenever used in this application the term "diameter" is meant to be the "average diameter", even if it is not specifically specified.

In the context of the present invention the term "ionisable" (or alternatively cationic) in the context of a compound or lipid means the presence of any uncharged group in said compound or lipid which is capable of dissociating by yielding an ion (usually an W ion) and thus itself becoming positively charged. Alternatively, any uncharged group in said compound or lipid may yield an electron and thus becoming negatively charged.

In the context of the present invention any type of ionizable lipid can suitably be used. Specifically, suitable ionizable lipids are ionizable amino lipids which comprise 2 identical or different tails linked via an S—S bond, each of said tails comprising an ionizable amine such as represented by In a specific embodiment, said ionisable lipid is a compound of formula (I):

$$\begin{array}{c} RCOO-X-CH_2CH_2-S \\ | \\ RCOO-X-CH_2CH_2-S \end{array} \quad (I)$$

wherein:

RCOO is selected from the list comprising: myristoyl, α-D-Tocopherolsuccinoyl, linoleoyl and oleoyl; and X is selected from the list comprising:

Such ionisable lipids are specifically represented by anyone of the following formulae:

More specifically, said ionisable lipid is a lipid of formula (I) wherein RCCO is α-D-Tocopherolsuccinoyl and X is such as represented by In the context of the present invention, the term "sterol", also known as steroid alcohol, is a subgroup of steroids that occur naturally in plants, animal and fungi, or can be produced by some bacteria. In the context of the present invention, any suitable sterol may be used, such as selected from the list comprising cholesterol, ergosterol, campesterol, oxysterol, antrosterol, desmosterol, nicasterol, sitosterol and stigmasterol; preferably cholesterol.

In the context of the present invention the term "phospholipid" is meant to be lipid molecule consisting of two hydrophobic fatty acid "tails" and a hydrophilic "head" consisting of a phosphate groups. The two components are most often joined together by a glycerol molecule, hence, in the phospholipid of the present invention is preferably a glycerol-phospholipid. Furthermore, the phosphate group is often modified with simple organic molecules such as choline (i.e. rendering a phosphocholine) or ethanolamine (i.e. rendering a phosphoethanolamine).

Suitable phospholipids within the context of the invention can be selected from the list comprising: 1,2-Dioleoyl-sn-glycero-3-phosphoethanolamine (DOPE), 1,2-Dioleoyl-sn-glycero-3-phosphocholine (DOPC), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhennisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachid onoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In a more specific embodiment, said phospholipid is selected from the list comprising: 1,2-Dioleoyl-sn-glycero-3-phosphoethanolamine (DOPE), 1,2-Dioleoyl-sn-glycero-3-phosphocholine (DOPC), and mixtures thereof.

In the context of the present invention, the term "PEG lipid" or alternatively "PEGylated lipid" is meant to be any suitable lipid modified with a PEG (polyethylene glycol) group. In a particular embodiment, said PEG lipid is selected from the list comprising: PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. More specific examples of such PEG lipids encompass C14-PEG2000 (1,2-Dimyristoyl-rac-glycerol, methoxypolyethylene glycol-2000 (DMG-PEG2000)) and C18-PEG5000 (1,2-Distearoyl-rac-glycerol, methoxypolyethylene glycol-5000 (DSG-PEG5000)).

In a specific embodiment of the present invention one or more of the following applies:
said LNP comprises about and between 35 mol % and 65 mol % of said ionisable lipid;
said LNP comprises about and between 15 mol % and 60 mol % of said sterol;
said LNP comprises about and between 0.5 mol % and 2 mol % of said PEG lipid; and/or
said LNP comprises about and between 5 mol % and 15 mol % of said phospholipid.

In another specific embodiment of the present invention one or more of the following applies:
said LNP comprises about and between 10 mol % and 60 mol % of said ionisable lipid;
said LNP comprises about and between 15 mol % and 50 mol % of said sterol;
said LNP comprises about and between 0.5 mol % and 10 mol % of said PEG lipid; and/or
said LNP comprises about and between 5 mol % and 40 mol % of said phospholipid.

In a more specific embodiment, one or more of the following applies:
said LNP comprises about and between 40 mol % and 60 mol % of said ionisable lipid;
said LNP comprises about and between 20 mol % and 40 mol % of said sterol;
said LNP comprises about and between 0.5 mol % and 5 mol % of said PEG lipid; and/or
said LNP comprises about and between 5 mol % and 15 mol % of said phospholipid.

Hence, in a particular embodiment, said LNP comprises about and between 10 mol % and 60 mol % of said ionisable lipid; preferably about and between 40 mol % and 60 mol %.

In yet another specific embodiment, said LNP comprises about and between 15 mol % and 50 mol % of sterol; preferably about and between 20 mol % and 40 mol %.

In a further embodiment, said LNP comprises about and between 0.5 mol % and 10 mol % of said PEG lipid; preferably about and between 0.5 mol % and 5 mol %.

In another specific embodiment, said LNP comprises about and between 5 mol % and 40 mol % of said phospholipid; preferably about and between 5 mol % and 15 mol %.

Hence, in a more specific embodiment, the LNP of the present invention comprises about and between 10 mol % and 60 mol % of said ionisable lipid; and/or about and between 15 mol % and 50 mol % of sterol; and/or about and between 0.5 mol % and 10 mol % of said PEG lipid; and/or about and between 5 mol % and 40 mol % of said phospholipid.

In another specific embodiment, the LNP of the present invention comprises about and between 40 mol % and 60 mol % of said ionisable lipid; and about and between 20 mol % and 40 mol % of sterol; and about and between 0.5 mol % and 5 mol % of said PEG lipid; and about and between 5 mol % and 15 mol % of said phospholipid.

The composition of particularly suitable LNP's in the context of the invention is represented in table 1:

TABLE 1

Composition of particularly suitable LNP's

| No | Ionizable Lipid (mol %) | Phospholipid (mol %) | Cholesterol (mol %) | PEG Lipid (mol %) | Type of Phospholipid | Type of PEG Lipid |
|---|---|---|---|---|---|---|
| 1 | 65 | 15 | 18 | 2 | DOPC | C14PEG2000 |
| 2 | 50 | 15 | 33 | 2 | DOPE | C14PEG2000 |
| 3 | 35 | 5 | 59.5 | 0.5 | DOPE | C18-PEG5000 |
| 4 | 65 | 5 | 28 | 2 | DOPC | C18-PEG5000 |
| 5 | 50 | 10 | 39 | 1 | DOPC | C14PEG2000 |
| 6 | 35 | 15 | 49.5 | 0.5 | DOPE | C14PEG2000 |
| 7 | 50 | 10 | 39 | 1 | DOPE | C18-PEG5000 |
| 8 | 50 | 5 | 44.5 | 0.5 | DOPC | C18-PEG5000 |
| 9 | 35 | 5 | 59 | 1 | DOPC | C14PEG2000 |
| 10 | 65 | 15 | 19 | 1 | DOPE | C18-PEG5000 |
| 11 | 35 | 15 | 49.5 | 0.5 | DOPC | C14PEG2000 |
| 12 | 50 | 10 | 39 | 1 | DOPE | C14PEG2000 |
| 13 | 65 | 5 | 29.5 | 0.5 | DOPC | C14PEG2000 |
| 14 | 35 | 15 | 48 | 2 | DOPE | C18-PEG5000 |
| 15 | 35 | 10 | 53 | 2 | DOPC | C18-PEG5000 |
| 16 | 35 | 5 | 58 | 2 | DOPE | C14PEG2000 |
| 17 | 65 | 5 | 28 | 2 | DOPE | C18-PEG5000 |
| 18 | 65 | 15 | 19.5 | 0.5 | DOPC | C18-PEG5000 |
| 19 | 65 | 10 | 24.5 | 0.5 | DOPE | C14PEG2000 |
| 20 | 50 | 10 | 39 | 1 | DOPC | C18-PEG5000 |

The inventors have found that the LNP's of the present invention are particularly suitable for the immunogenic delivery of nucleic acids; due to an increased targeting of the spleen in contrast to prior art known small LNP's which are mainly found to target the liver.

Hence the present invention provides LNP's comprising one or more nucleic acid molecules, such as DNA or RNA, more specifically mRNA.

A "nucleic acid" in the context of the invention is a deoxyribonucleic acid (DNA) or preferably a ribonucleic acid (RNA), more preferably mRNA. Nucleic acids include according to the invention genomic DNA, cDNA, mRNA, recombinantly produced and chemically synthesized molecules. A nucleic acid may according to the invention be in the form of a molecule which is single stranded or double stranded and linear or closed covalently to form a circle. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs. Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' untranslated region (5-UTR), a protein or peptide coding region and a 3' untranslated region (3'-UTR). mRNA has a limited halftime in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In a specific embodiment said mRNA molecules are mRNA molecules encoding immune modulating proteins.

In the context of the present invention, the term "mRNA molecules encoding immune modulating proteins" is meant to be mRNA molecules encoding proteins that modify the functionality of antigen presenting cells; more in particular dendritic cells. Such molecules may be selected from the list comprising CD40L, CD70, caTLR4, IL-12p70, EL-selectin, CCR7, and/or 4-1 BBL, ICOSL, OX40L, IL-21; more in particular one or more of CD40L, CD70 and caTLR4. A preferred combination of immunostimulatory factors used in the methods of the invention is CD40L and caTLR4 (i.e. "DiMix"). In another preferred embodiment, the combination of CD40L, CD70 and caTLR4 immunostimulatory molecules is used, which is herein also named "TriMix"

In another specific embodiment said mRNA molecules are mRNA molecules encoding antigen- and/or disease-specific proteins.

According to the present invention, the term "antigen" comprises any molecule, preferably a peptide or protein, which comprises at least one epitope that will elicit an immune response and/or against which an immune response is directed. Preferably, an antigen in the context of the present invention is a molecule which, optionally after processing, induces an immune response, which is preferably specific for the antigen or cells expressing the antigen. In particular, an "antigen" relates to a molecule which, optionally after processing, is presented by MHC molecules and reacts specifically with T lymphocytes (T cells).

In a specific embodiment, the antigen is a target-specific antigen which can be a tumor antigen, or a bacterial, viral or fungal antigen. Said target-specific antigen can be derived from either one of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target-specific antigen or its derived peptides.

To avoid any misunderstanding the LNP's of the present invention may comprise a single mRNA molecules, or they may comprise multiple mRNA molecules, such as a combination of one or more mRNA molecules encoding immune modulating proteins and/or one or more mRNA molecules encoding antigen- and/or disease-specific proteins.

In a very specific embodiment, said mRNA molecules encoding immunomodulatory molecules may be combined with one or more mRNA molecules encoding antigen- and/or disease-specific proteins. For example, the LNP's of the present invention may comprise mRNA molecules encoding the immunostimulatory molecules CD40L, CD70 and/or caTLR4 (such as Dimix or Trimix); in combination with one or more mRNA molecules encoding antigen- and/or disease-specific proteins. Thus, in a very specific embodiment, the LNP's of the present invention comprise an mRNA molecule encoding CD40L, CD70 and/or caTLR4; in combination with one or more mRNA molecules encoding antigen- and/or disease-specific proteins.

In a further aspect, the present invention provides a pharmaceutical composition comprising one or more LNP's as defined herein. Such pharmaceutical compositions are particularly suitable as a vaccine. Thus, the invention also provides a vaccine comprising one or more LNP's according to the present invention.

In the context of the present invention, the term "vaccine" as used herein is meant to be any preparation intended to provide adaptive immunity (antibodies and/or T cell responses) against a disease. To that end, a vaccine as meant herein contains at least one mRNA molecule encoding an antigen to which an adaptive immune response is mounted. This antigen can be present in the format of a weakened or killed form of a microbe, a protein or peptide, or an antigen encoding a nucleic acid. An antigen in the context of this invention is meant to be a protein or peptide recognized by the immune system of a host as being foreign, thereby stimulating the production of antibodies against is, with the purpose of combating such antigens. Vaccines can be prophylactic (example: to prevent or ameliorate the effects of a future infection by any natural or "wild" pathogen), or therapeutic (example, to actively treat or reduce the symptoms of an ongoing disease). The administration of vaccines is called vaccination.

The vaccine of the invention may be used for inducing an immune response, in particular an immune response against a disease-associated antigen or cells expressing a disease-associated antigen, such as an immune response against cancer. Accordingly, the vaccine may be used for prophylactic and/or therapeutic treatment of a disease involving a disease-associated antigen or cells expressing a disease-associated antigen, such as cancer. Preferably said immune response is a T cell response. In one embodiment, the disease-associated antigen is a tumor antigen. The antigen encoded by the RNA comprised in the nanoparticles described herein preferably is a disease-associated antigen or elicits an immune response against a disease-associated antigen or cells expressing a disease-associated antigen.

The LNP's and vaccines of the present invention are specifically intended for intravenous administration, i.e. the infusion of liquid substance directly into a vein. The intravenous route is the fastest way to deliver fluids and medications throughout the body, i.e. systemically. The present invention thus provides intravenous vaccines, as well as the use of the disclosed vaccines and LNP's for intravenous administration. The vaccines and LNP's of the present invention can thus be administered intravenously. The present invention also provides the use of the vaccines and LNP's according to the present invention; wherein the vaccine is administered intravenously.

The present invention also provides the LNP's, pharmaceutical compositions and vaccines according to this invention for use in human or veterinary medicine. The use of the LNP's, pharmaceutical compositions and vaccines according to this invention for human or veterinary medicine is also intended. Finally, the invention provides a method for the prophylaxis and treatment of human and veterinary disorders, by administering the LNP's, pharmaceutical compositions and vaccines according to this invention to a subject in need thereof.

The present invention further provides the use of an LNP, a pharmaceutical composition or a vaccine according to the present invention for the immunogenic delivery of said one or more nucleic acid molecules. This effect is specifically achieved using the larger LNP's of the invention, due to their preferential targeting to the spleen. The small-sized LNP's of the prior art where found to preferentially target the liver, thereby having little or no immunogenic effect. As such the LNP's, pharmaceutical compositions and vaccine of the present invention are highly useful in the treatment several human and veterinary disorders. Thus, the present invention provides the LNP's, pharmaceutical compositions and vaccines of the present invention for use in the treatment of cancer or infectious diseases.

In a further aspect, the present invention provides methods for the preparation of an LNP according to the present invention, comprising:
  preparing a first alcoholic composition comprising said ionisable lipid, said phospholipid, said sterol, said PEG lipid, and a suitable alcoholic solvent;
  preparing a second aqueous composition comprising said one or more nucleic acids and an aqueous solvent;
  mixing said first and second composition in a in a microfluidic mixing device using the following settings:
  Total Flow Rate (FR) of about 0.5 to about 8 ml/min, preferably of about 1 to 4 ml/min.
  Flow Rate Ratio (FRR) of about 1/1 to 5/1, preferably of about 2/1 to about 3/1

In further detail, the lipid components are combined in suitable concentrations in an alcoholic vehicle such as ethanol. Thereto, an aqueous composition comprising the nucleic acid is added, and subsequently loaded in a microfluidic mixing device.

The aim of microfluidic mixing is to achieve thorough and rapid mixing of multiple samples (i.e. lipid phase and nucleic acid phase) in a microscale device. Such sample mixing is typically achieved by enhancing the diffusion effect between the different species flows. Thereto several microfluidic mixing devices can be used, such as for example reviewed in Lee et al., 2011. A particularly suitable microfluidic mixing device according to the present invention is the NanoAssemblr from Precision Nanosystems.

The mixing parameters of such microfluidic mixing devices have a large impact on the characteristics of the obtained LNP's, specifically on the size thereof. Hence, to obtain large LNP's i.e. having an average diameter of at least 140 nm, preferably at least 200 nm, the FR and FRR parameters are highly relevant.

The total FR (Flow Rate) is a measure for the speed of microfluidic mixing and is in the prior art typically set at 8-12 ml/min to allow thorough mixing, thereby obtaining small LNP's for direction to the liver. In contrast, in the present invention, the FRW is set to be much lower, thereby obtaining larger LNP's suitable for use in the context of the invention.

The FRR (Flow Rate Ratio) is the ratio between lipids in the alcoholic phase and nucleic acids in the watery phase, and is in the invention typically set at about 2/1 to about 3/1.

EXAMPLES

Example 1

In this first example, the effect of particle size on the immunogenicity of mRNA LNP's was assessed. Thereto, 140 nm and 230 nm sized mRNA LNPs of identical composition were prepared. LNPs were composed of 50 mol % α-D-Tocopherolhemisuccinoyl (ionizable lipid), 10 mol % DOPE, 38,5 mol % cholesterol and 1.5 mol % DSG-PEG5000 (PEGylated lipid) at the indicated lipid ratio's (mol %). LNPs were produced on a Nano-Assemblr using different flow rates (FR; ml/min) and water/ethanol volume ratio's (FRR). 140 nm sized LNPs were produced at FR 4 ml/min whereas 230 nm sized LNPs were generated at FR 1 ml/min.

Figure 1:
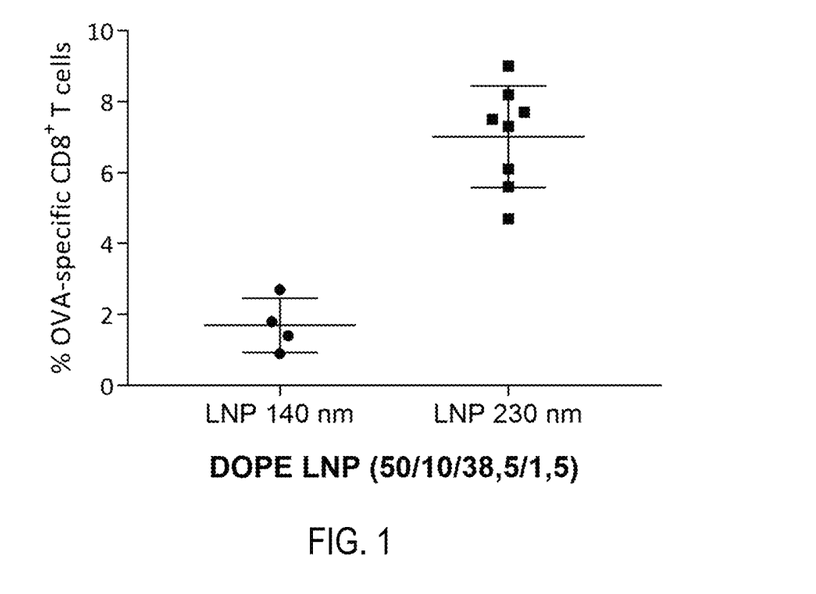
FIG. 1: Immunogenicity of 140 nm versus 230 nm sized mRNA LNPs of identical composition.

FIG. 1 shows the percentage of OVA-specific CD8+ T cells upon single intravenous administration in mice with OVA/TriMix mRNA LNPs (OVA: 10 µg; TriMix mRNA: 15 µg). As is very clear from FIG. 1, the immunogenicity of the larger LNP's is much higher compared to the immunogenicity of the smaller LNP's.

Example 2

Figure 2:
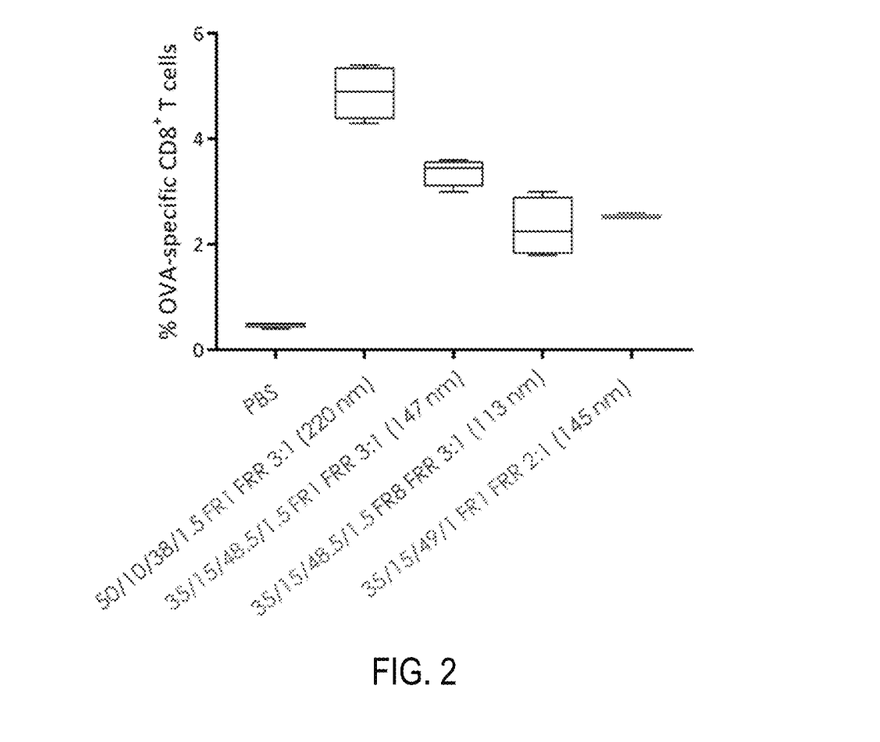
FIG. 2: Immunogenicity of OVA mRNA LNPs of different sizes after intravenous administration.

In this example, the immunogenicity of OVA mRNA LNPs of different size and composition after intravenous administration in mice was determined. All LNPs were composed of α-D-Tocopherolhemisuccinoyl (ionizable lipid), DOPE, cholesterol and DSG-PEG5000 at the indicated lipid ratio's (mol %), as defined in FIG. 2. LNPs were produced on a Nano-Assemblr using different flow rates (FR; ml/min) and water/ethanol volume ratio's (FRR), as also defined in FIG. 2. Percentages of OVA-specific CD8 T cells were quantified by flow cytometry 6 days post immunization. Again as is very clear from FIG. 2, the immunogenicity of the larger LNP's is higher compared to the immunogenicity of the smaller LNP's.

Example 3

Figure 3:
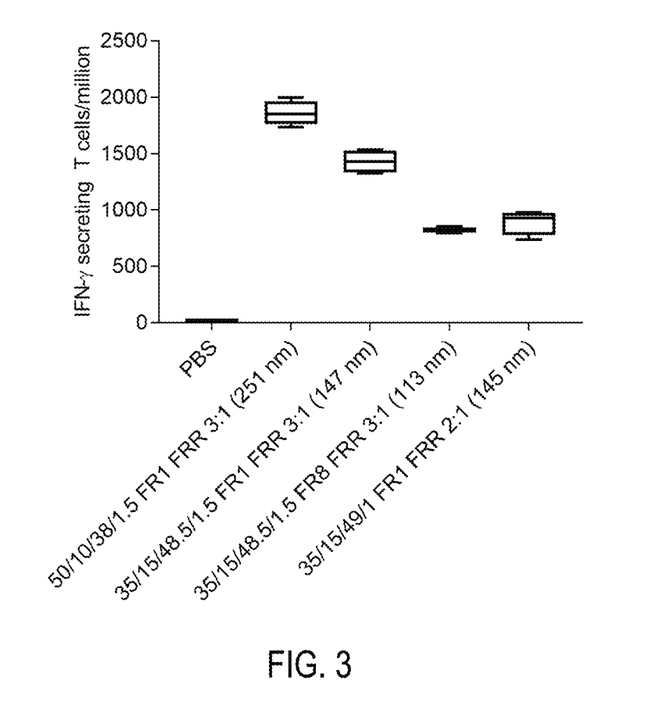
FIG. 3: Immunogenicity of OVA mRNA LNPs of different sizes after single intravenous administration.

In this example, the immunogenicity of OVA mRNA LNPs of different sizes and composition after single intravenous administration in mice was determined. The plot depicts the number of IFN-γ secreting CD8+ T cells/million splenocytes after restimulation of splenocytes with the OVA MHCI epitope SIINFEKL (5 µg/ml). All LNPs were composed of α-D-Tocopherolhemisuccinoyl (ionizable lipid), DOPE, cholesterol and DSG-PEG5000 at the indicated lipid ratio's (mol %), as defined in FIG. 3. LNPs were produced on a Nano-Assemblr using different flow rates (FR; ml/min) and water/ethanol volume ratio's (FRR), as also defined in FIG. 3. Percentages of OVA-specific CD8+ T cells were quantified by flow cytometry 6 days post immunization.

Example 4

Figure 4:
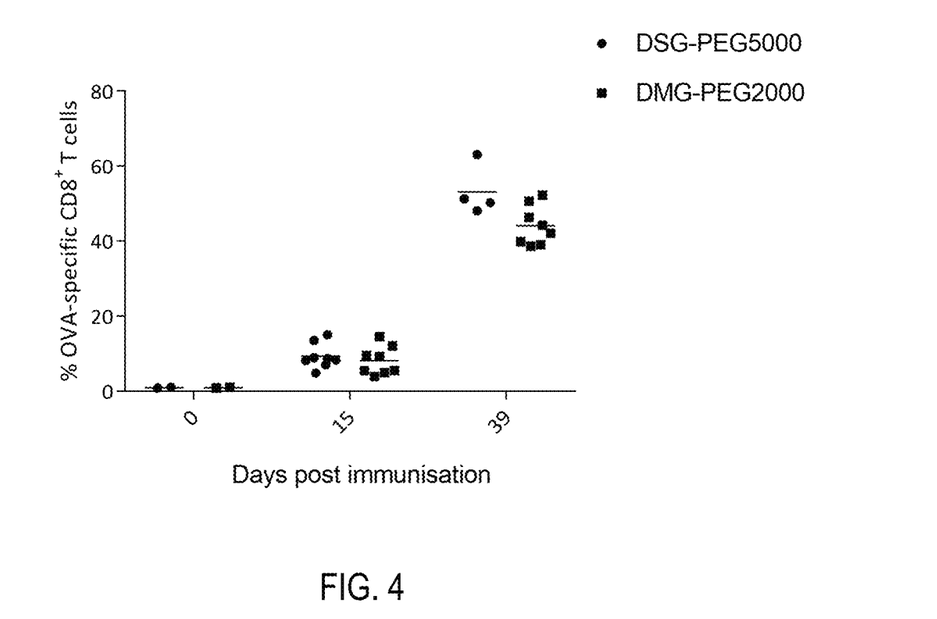
FIG. 4: Percentages of OVA specific T cells upon intravenous administration of large sized LNPs containing OVA mRNA (10 µg) and TriMix mRNA (15 µg).

Next, we assessed the effect of varying the PEGylated lipid, thereto, 2 different compositions were made either with DSG-PEG5000 or DMG-PEG2000. Percentages of OVA specific T cells upon intravenous administration of large sized LNPs containing OVA mRNA (10 µg) and TriMix mRNA (15 µg) was determined and represented in FIG. 4. Mice were immunized at day 0 and day 20. % OVA-specific T cells were assessed on blood samples at days 15 and 39. As is evident from FIG. 4, the type of PEGylated lipid has no effect on the immunogenicity of the LNP's.

Example 5

Figure 5:
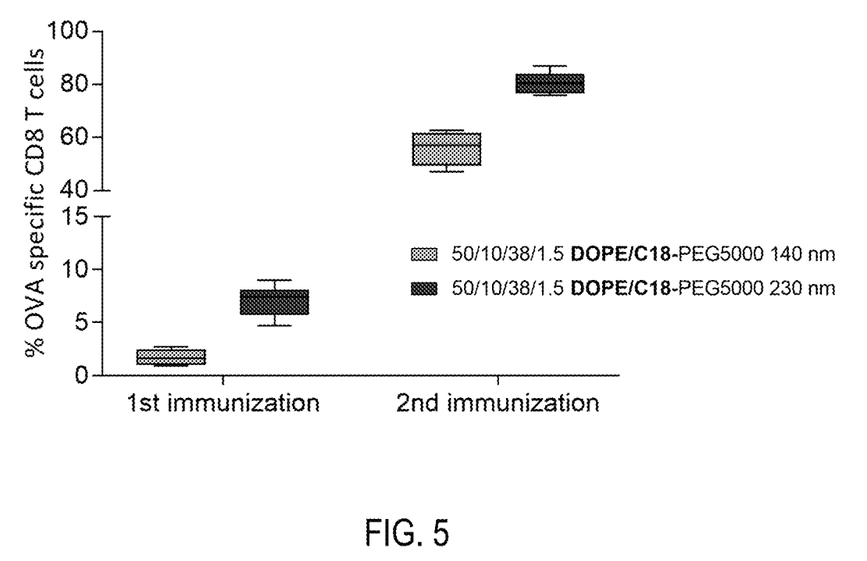
FIG. 5: Comparison of the immunogenicity of 140 nm and 230 nm sized mRNA LNPs after one and two intravenous administrations of mRNA LNPs.

In this example, we assessed, the immunogenicity of small and large LNP's after repeated immunization, using 140 nm and 230 nm sized mRNA LNPs (FIG. 5). LNPs were composed of 50 mol % α-D-Tocopherolhemisuccinoyl (ionizable lipid), 10 mol % DOPE (phospholipid), 38 mol % cholesterol and 1.5 mol % DSG-PEG5000 at the indicated lipid ratio's (mol %), as defined in FIG. 5. LNPs contained 10 μg of OVA mRNA and 15 μg of TriMix mRNA (CD40L, CD70 and caTLR4). Percentages of OVA-specific CD8 T cells responses were measured five days post immunization.

Example 6

Figure 6:
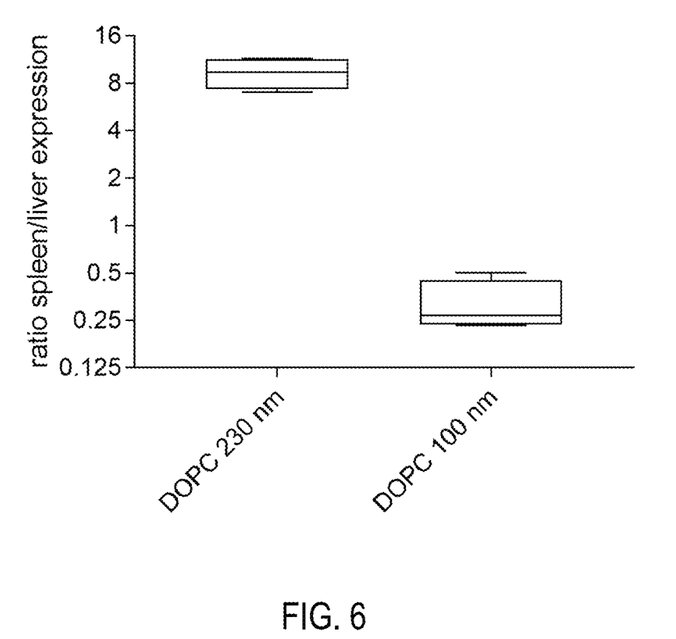
FIG. 6: Comparison ratio spleen/liver expression of 100 nm and 230 nm sized mRNA LNPs

In this example, we compared mRNA expression in spleen and liver after intravenous injection of mice with Fluc mRNA LNPs of different size—FIG. 6). LNPs were composed of α-D-Tocopherolhennisuccinoyl (ionizable lipid), DOPC, cholesterol and DSG-PEG5000 at respective lipid ratios of 50/10/38.5/1.5. LNPs of differential sizes were generated by using different flow rates of microfluidic mixing (FR1 versus FR4). The figure depicts the ratio of spleen to liver expression of Fluc mRNA, measured by in vivo bioluminescence of ph/s/cm²/sr.

Example 7

Figure 7A:
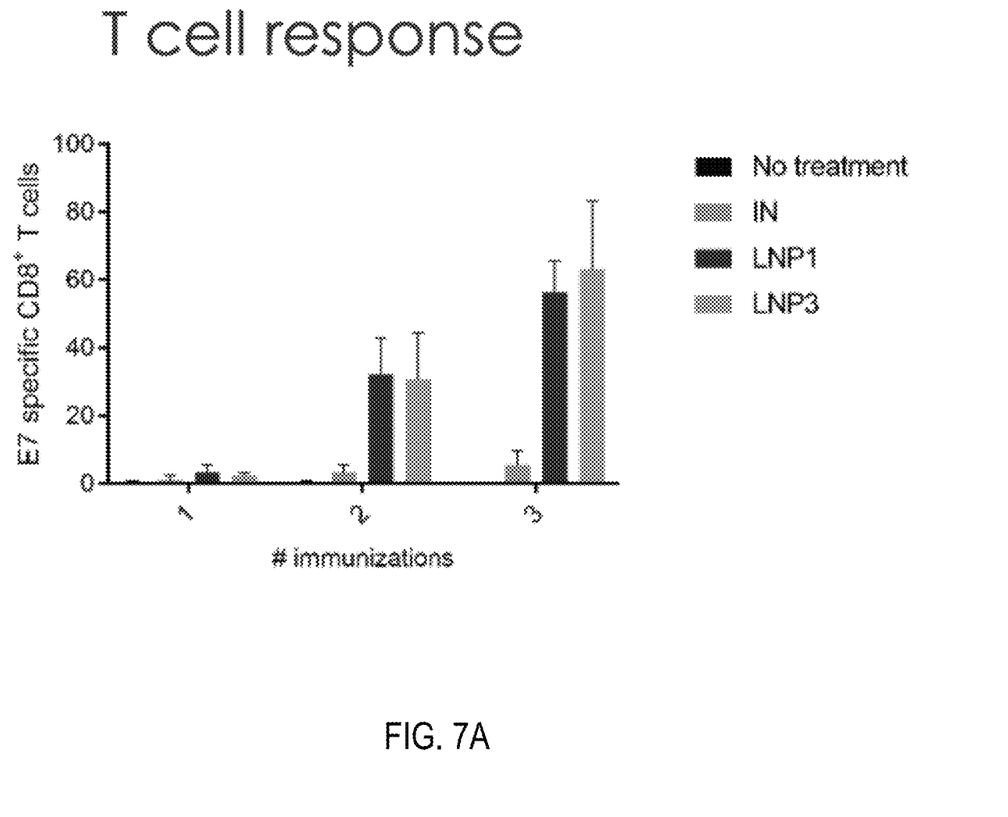
FIGS. 7A and 7B: Comparisons of intravenous LNP mRNA vs intranodal administration.
Figure 7B:
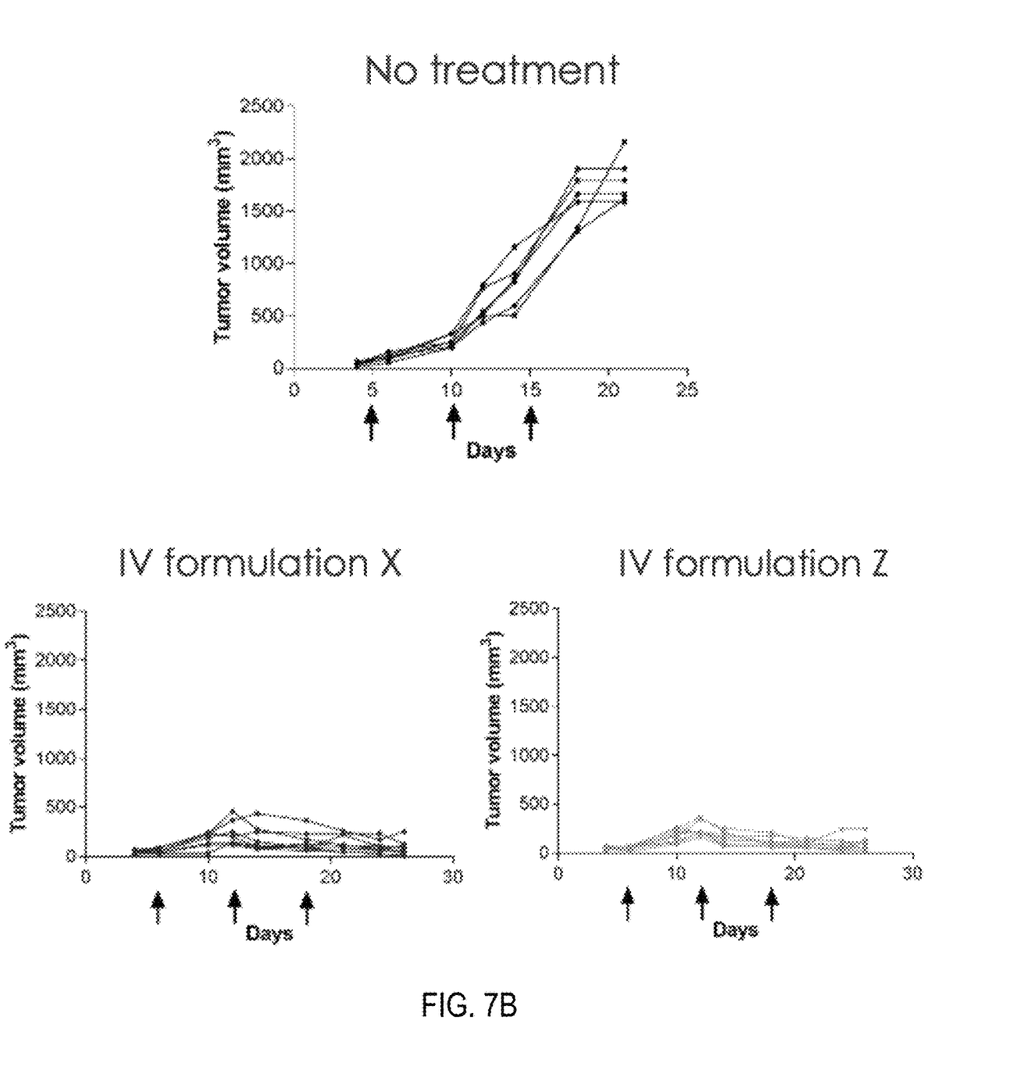

In this example, we demonstrate that formulated intravenous mRNA LNPs evoke superior immunogenicity and anti-tumor efficacy compared to intranodal approaches.
The characteristics of the used API are as follows:
E7 mRNA, column purified, 10 μg/administration
Immunization schedule: 3 times weekly
The results of this experiment are shown in FIGS. 7A and 7B, which clearly show that the used intravenous approach using mRNA LNPs is superior over the intranodal approach, both in terms of immunogenicity and anti-tumor efficacy. Moreover, there appears to be a correlation between the magnitude of the T cell response and the anti-tumor efficacy.

Example 8

Figure 8:
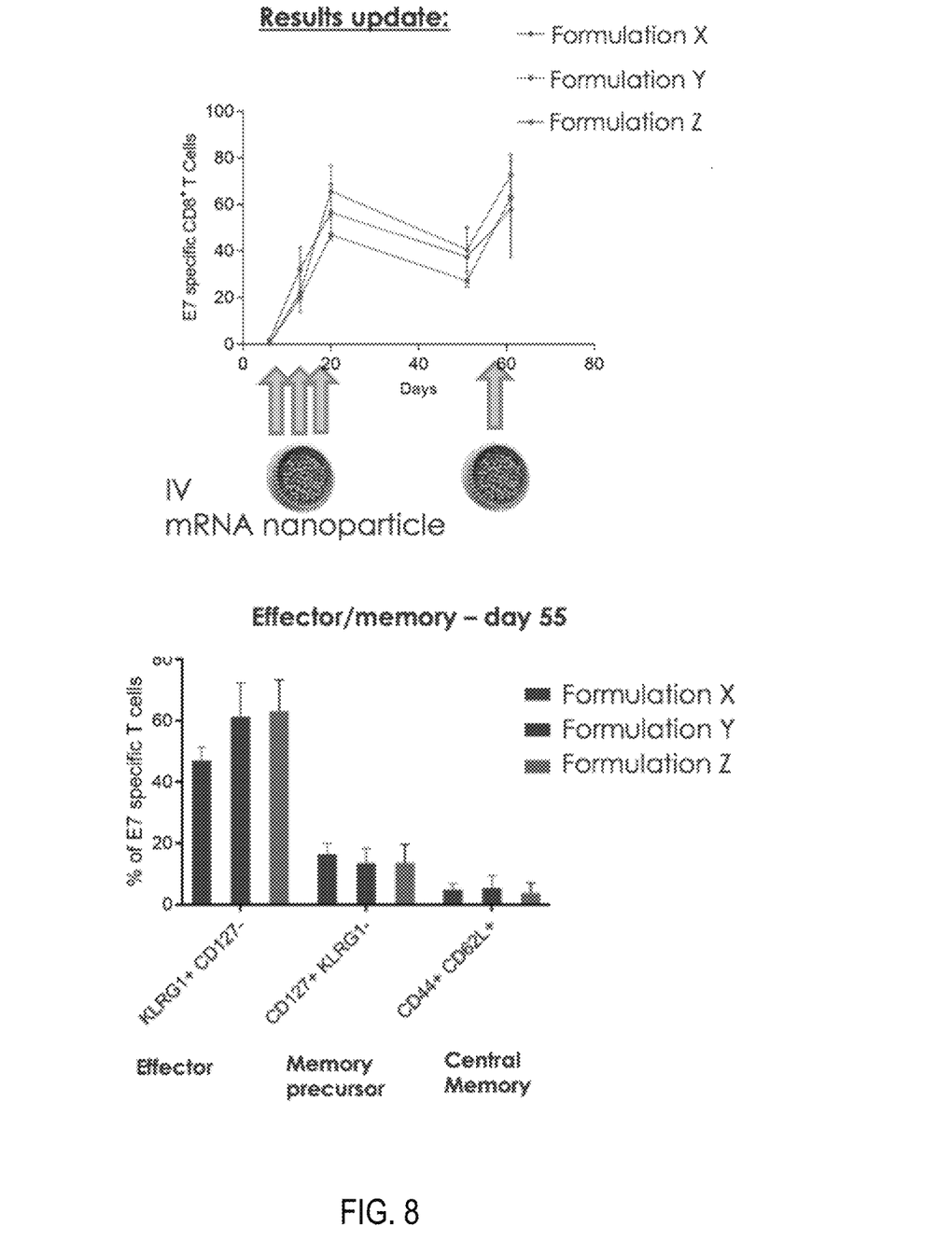
FIG. 8: T cell responses to LNP mRNA formulations are long-live and boostable.

In this example, we demonstrate that T cell responses to mRNA LNP formulations are long-lived and boostable.
Thereto, 3 different formulations where used in the immunization schedules of which the results are shown in FIG. 8. From these results, the following observations/conclusions can be made:
Extended contraction phase with high % of E7-specific T cells 40 days after immunization 3
Memory conversion
Stunning recall response: IV formulation vaccines can be boosted.

Example 9

Figure 9:
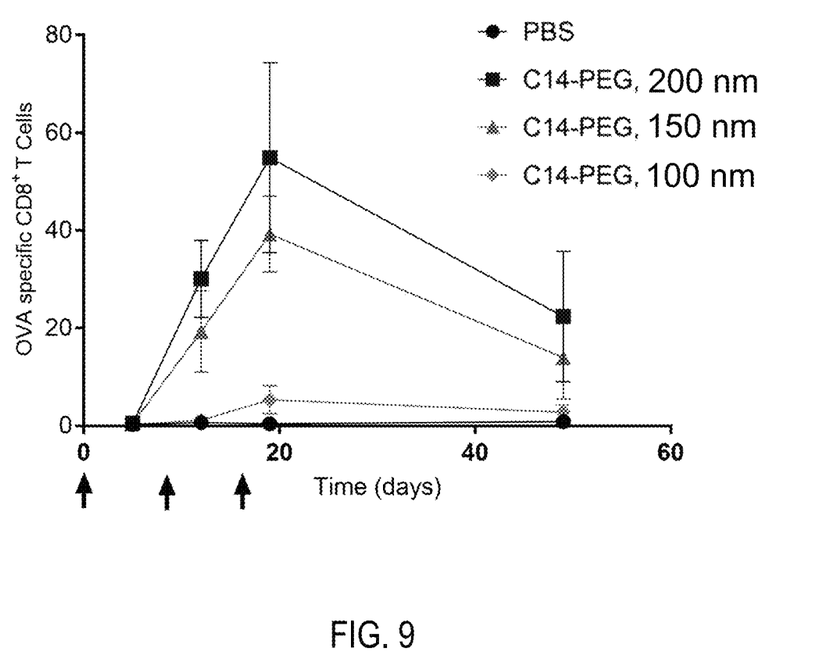
FIG. 9: Comparison of immunogenicity and T cell response of LNPs having average sizes of 150 nm or 200 nm with LNPs having average size of 100 nm.

In this example, a further experiment demonstrating the effect of the size of the LNPs was performed.
Thereto, the following experimental settings were used:
Ratio ionizable lipid/chol/DOPE/DMG-PEG2000-50/38.5/10/1.5
Three immunizations IV; days 0, 7, 14
mRNA: OVA encoding mRNA, 10 μg/immunization
Assessment of % OVA specific CD8 T cells at days 5, 12, 19 and 50 after 1$^{st}$ immunization
The results are detailed in FIG. 9, and clearly show that LNPs having an average size of 150 nm or 200 nm are clearly much more immunogenic in terms of the T cell response, compared to LNPs having an average size of only 100 nm.

REFERENCES

Reichmuth et al., 2016—mRNA vaccine delivery using lipid nanoparticles—Therapeutic Delivery Vol. 7, N° 5.
Li et al., 2015—An Orthogonal Array Optimization of Lipid-like Nanoparticles for mRNA Delivery in Vivo—Nano Letters 15(12) pg. 8099-8107.
Thess et al., 2015—Sequence-engineered mRNA without Chemical Nucleoside Modifications Enables an Effective Protein Therapy in Large Animals—Molecules Therapy Vol. 23, Issue 9 pg. 1456-1464.
Kauffman et al., 2016—Materials for non-viral intracellular delivery of messenger RNA therapeutics—Journal of Controlled Release, Vol. 240, pg. 227-234.
Richner et al., 2017—Modified mRNA vaccines protect against Zika virus infection—Cell, Vol. 168, Issue 6 pg. 1114-1125
Liang et al., 2017—Efficient Targeting and Activation of Antigen-Presenting Cells In Vivo after Modified mRNA Vaccine Administration in Rhesus Macaques—Molecular Therapy, vol. 25 Issue 12 pg. 2635-2647.
Lee et al., 2011—Microfluidic Mixing: A Review—Int. J. Mol. Sci. 12(5): pg. 3263-3287.

The invention claimed is:
1. A mixture of lipid nanoparticles, the lipid nanoparticles in the mixture comprising:
from about 35 mol % to about 65 mol % of an ionizable lipid;
from about 5 mol % to about 15 mol % of a phospholipid selected from the group consisting of DOPE, DOPC, and mixtures thereof;
from about 15 mol % to about 50 mol % of a sterol;
from about 0.5 mol % to about 2 mol % of a PEG lipid; and
one or more mRNA molecules,
wherein the lipid nanoparticles of the mixture have average diameters of from about 160 nm to about 230 nm to target the spleen in preference over the liver at a ratio of about 8 to 1 when administered intravenously; and
wherein the ionisable lipid is a compound of formula (I):

wherein:
RCOO is alpha-D-Tocopherolsuccinoyl; and
X is

2. The mixture of lipid nanoparticles of claim 1, wherein the sterol is selected from the group consisting of cholesterol, ergosterol, campesterol, oxysterol, antrosterol, desmosterol, nicasterol, sitosterol, and stigmasterol.
3. The mixture of lipid nanoparticles of claim 1, wherein the sterol is cholesterol.
4. The mixture of lipid nanoparticles of claim 1, wherein the PEG lipid is selected from the group consisting of PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

5. The mixture of lipid nanoparticles of claim 1, wherein the lipid nanoparticles comprise from about 40 mol % to about 60 mol % of the ionizable lipid.

6. The mixture of lipid nanoparticles of claim 1, wherein the lipid nanoparticles comprise from about 20 mol % to about 40 mol % of the sterol.

7. The mixture of lipid nanoparticles of claim 1, wherein:
the lipid nanoparticles comprise from about 40 mol % to about 60 mol % of the ionizable lipid; and
the lipid nanoparticles comprise from about 20 mol % to about 40 mol % of the sterol.

8. The mixture of lipid nanoparticles of claim 7, wherein the one or more mRNA molecules are selected from the group consisting of immunomodulatory polypeptide-encoding mRNA, antigen-encoding mRNA, and combinations thereof.

9. The mixture of lipid nanoparticles of claim 7, wherein the one or more mRNA molecules are immunomodulatory-encoding mRNA selected from the group consisting of mRNA encoding for CD40L, CD70, caTLR4, and combinations thereof.

10. A pharmaceutical composition or a vaccine comprising:
the mixture of lipid nanoparticles according to claim 1; and
a pharmaceutically acceptable carrier.

11. A human or veterinary medicine comprising the mixture of lipid nanoparticles according to claim 1, optionally in combination with a pharmaceutically acceptable carrier.

12. A mixture of lipid nanoparticles, the lipid nanoparticles in the mixture comprising:
from about 35 mol % to about 65 mol % of an ionizable lipid;
from about 5 mol % to about 15 mol % DOPC;
from about 15 mol % to about 50 mol % of a sterol;
from about 0.5 mol % to about 2 mol % of a PEG-modified diacylglycerol; and
one or more mRNA molecules,
wherein the lipid nanoparticles of the mixture have average diameters of about 230 nm to target the spleen in preference over the liver at a ratio of about 8 to 1 when administered intravenously; and
wherein the ionizable lipid is a compound of formula (I):

with RCCO being α-D-Tocopherolsuccinoyl: and
X being

13. The mixture of lipid nanoparticles of claim 12, wherein the lipid nanoparticles of the mixture are products of mixing an alcoholic composition and an aqueous composition in a microfluidic mixing device set to a Total Flow Rate (FR) from about 0.5 mL/min to about 8 mL/min and a Flow Rate Ratio (FRR) from about 2/1 to 3/1 of lipids from the alcoholic composition to nucleic acids in the aqueous composition, the alcoholic composition comprising the ionizable lipid, the phospholipid, the sterol, and the PEG-modified diacylglycerol, the aqueous composition comprising the one or more mRNA molecules.

14. A mixture of lipid nanoparticles, the lipid nanoparticles in the mixture comprising:
from about 35 mol % to about 65 mol % of an ionizable lipid;
from about 5 mol % to about 15 mol % DOPE;
from about 15 mol % to about 50 mol % of a sterol;
from about 0.5 mol % to about 2 mol % of a PEG-modified diacylglycerol; and
one or more mRNA molecules,
wherein the lipid nanoparticles of the mixture have average diameters of about 160 nm to target the spleen in preference over the liver when administered intravenously; and
wherein the ionizable lipid is a compound of formula (I):

with RCCO being alpha-D-Tocopherolsuccinoyl; and
X being

15. A method for inducing an immune response in a mammal against an mRNA encoded antigen, the method comprising:
administering to the mammal by intravenous injection a composition comprising the mixture of lipid nanoparticles according to claim 1 wherein the one or more mRNA molecules encode an antigen, optionally in combination with a pharmaceutically acceptable carrier.

16. A method for treating a cancer or an infectious disease, the method comprising:
administering to a subject in need thereof by intravenous injection a composition comprising the mixture of lipid nanoparticles according to claim 1, optionally in combination with a pharmaceutically acceptable carrier.

* * * * *

UNITED STATES PATENT AND TRADEMARK OFFICE
CERTIFICATE OF CORRECTION

PATENT NO. : 11,684,577 B2
APPLICATION NO. : 16/961843
DATED : June 27, 2023
INVENTOR(S) : Stefaan De Koker, Sanne Bevers and Peter Tomme It is certified that error appears in the above-identified patent and that said Letters Patent is hereby corrected as shown below:

On the Title Page

Column 2, item (57), abstract, Line(s) 2, delete "(LPN)" and insert --(LNP)--, therefor.

In page 2, Column 1, item (56), other publications, cite no. 3, delete "345-301" and insert --345-351--, therefor.

In page 2, Column 2, item (56), other publications, cite no. 9, delete "Modicfied" and insert --Modified--, therefor.

In the Specification

In Column 4, Line(s) 4, delete "making" and insert --makes--, therefor.

In Column 5, Line(s) 16, delete "W ion" and insert --$H^+$ ion--, therefor.

In Column 7, Line(s) 49, delete "animal" and insert --animals--, therefor.

In Column 8, Line(s) 25, delete "palmnitoyl" and insert --palmitoyl--, therefor.

In Column 8, Line(s) 28, delete "cholesterylhennisuccinoyl" and insert --cholesterylhemisuccinoyl--, therefor.

In Column 10, Line(s) 45, after "nucleic", insert --acid--.

In Column 11, Line(s) 61, delete "molecules" and insert --molecule--, therefor.

In Column 13, Line(s) 13, after "treatment", insert --of--.

In Column 15, Line(s) 7, delete "Percentanges" and insert --Percentages--, therefor.

Signed and Sealed this
Twenty-sixth Day of September, 2023

Katherine Kelly Vidal
*Director of the United States Patent and Trademark Office*

In Column 15, Line(s) 15, delete "Tocopherolhennisuccinoyl" and insert --Tocopherolhemisuccinoyl--, therefor.

In Column 15, Line(s) 42, delete "where" and insert --were--, therefor.

In the Claims

In Column 16, Line(s) 38, Claim 1, after "diameters", delete "of".

In Column 18, Line(s) 48, Claim 15, after "claim 1", insert --,--.